_United States Patent_ [19]

Brattsand et al.

[11] 3,996,359

[45] * Dec. 7, 1976

[54] NOVEL STEREOISOMERIC COMPONENT A OF STEREOISOMERIC MIXTURES OF 2'-UNSYMMETRICAL 16,17-METHYLENEDIOXY STEROID 21-ACYLATES, COMPOSITIONS THEREOF, AND METHOD OF TREATING THEREWITH

[75] Inventors: Ralph Lennart Brattsand; Bo Thuresson af Ekenstam, both of Molndal; Karl Göran Claeson, Goteborg; Bror Arne Thalén, Molndal, all of Sweden

[73] Assignee: AB Bofors, Bofors, Sweden

[ * ] Notice: The portion of the term of this patent subsequent to Dec. 23, 1992, has been disclaimed.

[22] Filed: Nov. 6, 1975

[21] Appl. No.: 629,493

Related U.S. Application Data

[63] Continuation-in-part of Ser. No. 359,913, May 14, 1973, Pat. No. 3,928,326.

[30] Foreign Application Priority Data

May 19, 1972 Sweden .............................. 6645/72

[52] U.S. Cl. ...................... 424/241; 260/239.55 D
[51] Int. Cl.² ...................................... A61K 31/58
[58] Field of Search ........... 424/241; 260/239.55 D

[56] References Cited
UNITED STATES PATENTS

| 3,758,524 | 9/1973 | Anner et al. ............. 260/239.55 D |
| 3,951,958 | 4/1976 | Prezewowsky et al. ... 260/239.55 D |

_Primary Examiner_—Elbert L. Roberts
_Attorney, Agent, or Firm_—Gordon W. Hueschen

[57] ABSTRACT

A process for the resolution of stereoisomeric mixtures of certain steroids obtained by synthesis into its components, comprising subjecting the stereoisomeric mixture to gel filtration, the components in view of different retention volumes being separated and being separately recoverable; and stereoisomeric components A and B thereby obtained, pharmaceutical compositions thereof; and method of treating inflammation therewith.

61 Claims, No Drawings

NOVEL STEREOISOMERIC COMPONENT A OF STEREOISOMERIC MIXTURES OF 2'-UNSYMMETRICAL 16,17-METHYLENEDIOXY STEROID 21-ACYLATES, COMPOSITIONS THEREOF, AND METHOD OF TREATING THEREWITH

This application is a continuation-in-part of our prior-filed, co-pending application Ser. No. 359,913, filed May 14, 1973, now U.S. Pat. No. 3,928,326.

This application claims the 21-acylates of Component A of the novel steroid stereoisomeric mixtures, pharmaceutical compositions thereof and method of treating therewith. Such compounds and compositions have distinctive characteristics with respect to the corresponding Component B 21-esters and compositions thereof, as set forth in Table 4 of this application and in the text immediately preceding said Table.

The present invention refers to a process for the separation of a stereoisomeric mixture of certain steroids obtained by synthesis into its components, below called component A and component B. The invention also refers to stereoisomeric components A and B thereby obtained, pharmaceutical compositions thereof and method of treating inflammation therewith.

It is a well-known fact that mixtures of stereoisomers having the same molecular weight and in other respects possessing practically identical solubility characteristics may be extremely difficult to separate. It is, therefore, highly surprising that in conformity with the present invention it has been shown possible to separate the stereoisomeric components by gel filtration. The gel filtration technique is normally used to separate molecules having a lower molecular weight from molecules having a higher molecular weight. Stereoisomers, the molecules of which have the same molecular weight, and therefore not expected to have the same retention volume in gel filtration in view of which they would thus not be separable by this procedure. Therefore, it was most surprising that the stereoisomeric components A and B having the same molecular weight may still be separated with excellent result using this procedure.

The separation process according to the present invention has made it possible to investigate the physiological characteristics of the separated stereoisomeric components. In this connection it has surprisingly been found that one of the stereoisomeric components, component B, has consistently physiologically better characteristics than the other stereoisomeric component, component A, and that it is also better than the original mixture in this respect. Thus it is possible by the process of the present invention to prepare in a pure form new stereoisomeric components, which have certain advantages over the original synthetic stereoisomeric mixtures.

More precisely, the present invention refers to steroids having the general formula:

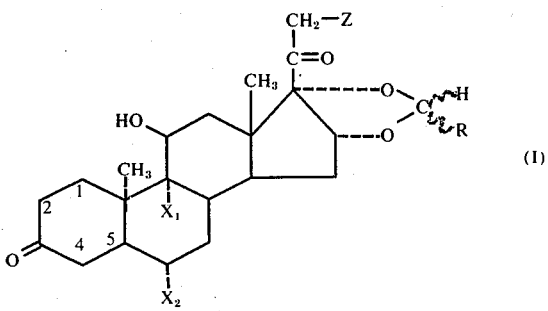

(I)

wherein the 1,2 and 4,5-positions are saturated or a double bond is present in at least one of said two positions, R is a straight or branched alkyl having 1-10, preferably 1-6 carbon atoms, $X_1$ and $X_2$ are independently selected from hydrogen and fluorine, $X_1$ being selected from hydrogen and fluorine when $X_2$ is hydrogen and $X_1$ being fluorine when $X_2$ is fluorine, Z is hydroxyl, possibly esterified, preferably having a maximum of 12 carbon atoms, if any, in the esterifying group. The individual stereoisomeric components present in a mixture of a steroid having the above formula I may be elucidated in the following way:

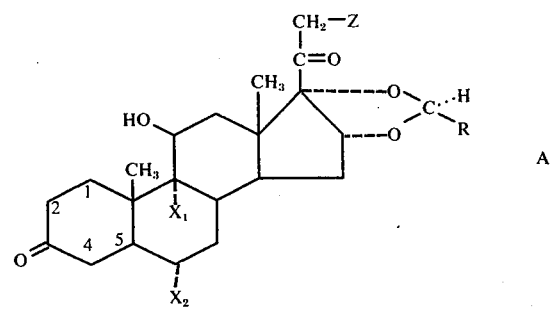

and

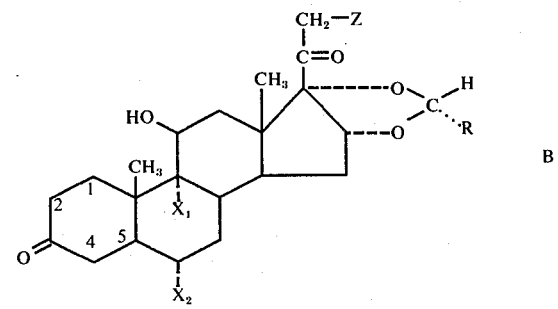

In the above formulas the stereoisomeric components differ from each other with regard to the space orientation about the 2'-carbon atom in the dioxolane ring.

As introductorily indicated the process according to the invention consists in subjecting a stereoisomeric mixture or a stereoisomeric pair of steroids having the above formula I to gel filtration, the stereoisomeric components A and B being separated in view of different retention volumes and being separately recoverable. The gel filtration may be carried out on many different types of gel materials. One type of such materials is hydroxypropylated cross-linked dextrane gels on the type Sephadex LH, for instance Sephadex LH 20 sold by Pharmacia Fine Chemicals, Uppsala, Sweden, resulting in a good fractionation within the molecular weight range 100-4000. Another useful gel type consists of copolymers of vinyl acetate having such exclusion limits as to be useful in the molecular weight range up to about 1000. One such vinyl acetate gel useful in this connection is Merckogel, type OR PVA 2000 sold by AG E. Merck, Darmstadt, Western Germany. The gel material is used as equilibrium with a suitable solvent. As an eluting agent halogenated hydrocarbons, ethers or esters or mixtures thereof, may be used, and chloroform, methylene chloride, ethylene chloride tetrahydrofurane, dioxane and ethyl acetate have been used successfully. Hereby an excellent separation of stereoisomer A from stereoisomer B will be obtained, and the stereoisomeric mixture A, B may, of course, also in an excellent way be removed from by-products formed in the steroid synthesis.

In formula I above the hydroxyl group in 21-position may be esterified with a fatty acid. Such fatty acid may have a straight or branched hydrocarbon chain and preferably contain 1-12 carbon atoms. As examples of suitable acids acetic acid, propionic acid, butyric acid, valeric acid, isovaleric acid, trimethyl acetic acid, hexanoic acid, tert.-butylacetic acid, octanoic acid may be used. It may also be esterified with a heterocyclic carboxylic acid, for instance pyridine-3-, pyridine-4-, and benzofurane-2-carboxylic acids; or methoxymethyl carboxylic acid. For the preparation of water-soluble derivatives the esterification may be carried out with dicarboxylic acids having preferably 2 to 12 carbon atoms, or with phosphoric or sulphuric acids.

The steroids I in the form of cyclic acetals may be synthesized in a manner known per se starting from the 16α, 17α-dihydroxy steroids and an aldehyde in the presence of an acid catalyst, for instance perchloric acid, p-toluene, sulphonic acid, hydrochloric acid etc., in dioxane or another suitable solvent. The reaction results in a mixture of stereoisomers, A and B, having the same molecular weight and practically identical solubility characteristics, and the stereoisomers have been found to be extremely difficult to separate by conventional methods for the separation of stereoisomers, for instance by recrystallization.

The invention will now be further illustrated by non-limiting examples. In the examples there is used for the chromatography a column having a length of 85 cm, an inner diameter of 2.5 cm, the flow rate being 1 ml/min. The retention volumes given in the examples refer to chloroform as eluting agent.

In the gel filtration on the column it has been found to be easier to separate the by-products from the isomeric mixture in the crude product than to separate the isomers from each other, since the former show greater differences in retention volumes than the latter. It has also been found that the solubility of the crude product as well as the solubility of the purified isomeric mixture decreases, whereas the separation decree increases with decreasing polarity of the solvents used. This is particularly true with regard to the derivatives substituted with a shorter side chain on the 2'-carbon atom of the dioxolane ring. In the chromatographic separation of the examples below it has therefore turned out to be advantageous first to separate the isomeric mixture from the by-products of the crude product by means of a somewhat more polar solvent and then to separate the isomers from each other by means of a solvent possessing a lower polarity. This results in several advantages. Firstly, the whole capacity of the column may be utilized and great amounts of crude product may be freed from by-products in each application. Secondly, a possible partial use of the column capacity resulting from limitations in the solubility of the isomeric mixture in the solvents having a lower polarity may be compensated by making new test applications on the column at relatively short intervals day and night without awaiting the previous application to leave the column. The solvents which have been found to be highly active in the pre-separation, such as methylene chloride, ethylene chloride, tetrahydrofurane and ethyl acetate, have also given completely satisfactory isomeric separation, whereas chloroform and dioxane have given an even better result with regard to the isomers most difficult to separate.

In all examples the molecular weights are determined by mass spectroscopy, and in all NMR-investigations tetramethylsilane has been used as an internal reference. All melting points have been determined by means of a Reichert melting point microscope.

EXAMPLE 1

16α, 17α-(2'-Hydrogen-2'methyl)-methylene dioxy-9-fluorpregna-1,4-diene-11β, 21-diol-3,20-dione.

To a solution of 112.0 mg newly distilled paraldehyde and 0.2 ml 72% perchloric acid in 75 ml well purified and dried dioxane 500.0 mg of triamcinolon were added in portions for 40 minutes. The reaction mixture was stirred for further 5.5 hours at room temperature, and was then diluted with 200 ml methylene chloride. The solution was washed twice with a 15% sodium bicarbonate solution and three times with water and dried. The solvents were evaporated in vacuum and the residue was taken up in ether and precipitated with petroleum ether. The dried crude product (533.0 mg) was chromatographed on a column packed with hydroxypropylated, cross-linked dextran gel (Sephadex LH-20, molecular weight range 100-4000; Pharmacia Fine Chemicals, Uppsala, Sweden) using methylene chloride as an eluting agent. This resulted in 431.7 mg (81%) pure isomeric mixture having the following characteristics: Melting point about 207°–222° C; $[\alpha]_D^{25} = +107.2°$ ($c=0.3$ in $CH_2Cl_2$), molecular weight = 420 (theor. 420.5).

The isomeric mixture (338.2 mg) was rechromatographed on a column packed with Sephadex LH 20 and using chloroform as an eluting agent. Two different isomers, A and B, of 16α, 17α-(2'-hydrogen-2'-methyl) methylene dioxy-9-fluorpregna-1,4-diene-11β-21-diol-3,20-dione were obtained in the following yields and having the following characteristics: A: 123.4 mg (37%); melting point 217°–19° C; $[\alpha]_D^{25} = +87.5°$ ($c=0.3$ in $CH_2Cl_2$); molecular weight = 420 (theor. 420.5) (Retention volume 920–990 ml). B: 194.7 mg (58 %); melting point 224°–28° C; $[\alpha]_D^{25} = +120.8°$ ($c=0.3$ in $CH_2Cl_2$); molecular weight = 420 (theor. 420.5) (Retention volume 1020–1100 ml). The isomer purity (>98%) of A and B was determined by NMR spectroscopy by studying the signal for 18-$CH_3$ positioned at $\delta = 1.00$ ppm ($CDCl_3$) for A and at $\delta = 0.92$ ppm ($CDCl_3$) for B.

Similar separation results have been obtained by using a gel of copolymers of vinyl acetate (Merckogel OR-PVA 2000 molecular weight range up to 1000; AG E. Merck, Darmstadt, Western Germany), as well as by using, in addition to chloroform and methylene chloride, ethylene chloride, ethyl acetate, tetrahydrofurane and dioxane as eluting agents on both types of gel materials.

EXAMPLES 2–15

Analogous to the process described in Example 1 different isomeric mixtures were prepared, the isomers given in Table 1 below being obtained by means of separation according to Example 1. The NMR-investigations were carried out in $CDCl_3$ if not otherwise stated.

using chloroform as an eluant. Two different isomers, A and B, of 16α, 17α-(2′-hydrogen-2′-methyl)methylenedioxy-11β-hydroxy-21-(benzofurane-2-carbonyloxy)-9-fluorpregna-1,4-dione-3,20-dione were obtained in the following yields and having the following characteristics:

A: 28.1 mg (35%); melting point 250°–56° C; $[\alpha]_D^{25} = +158.9°$ ($c = 0.2$ in $CH_2Cl_2$); molecular weight = 564 (theor. 564.6). Retention volume 270–90 ml.

B: 24.2 mg (30%); melting point 247°–50° C; $[\alpha]_D^{25} = +168.3°$ ($c = 0.2$ in $CH_2Cl_2$); molecular weight = 564

Table 1

| Ex. No. | The 16α, 17α-derivative of | with | Isomer | $[\alpha]_D^{25}$ (c=0.2 in $CH_2Cl_2$) | Mp (° C) | Molecular weight found | Molecular weight calculated | 18-$CH_3$ δ (ppm) | Retention volume (ml) |
|---|---|---|---|---|---|---|---|---|---|
| 2 | triamcinolone | propionaldehyde | A | +85.1° | 204–7 | 434 | 434.5 | 0.99 | 840–862 |
|   |   |   | B | +112.7° | 189–92 | " | " | 0.933 | 924–990 |
| 3 | " | n-butyraldehyde | A | +77.5° | 150–5 | 448 | 448.5 | 1.00 | 822–876 |
|   |   |   | B | +105.5° | 147–50 | " | " | 0.93 | 912–984 |
| 4 | " | n-valeric aldehyde | A | +73.7° | 123–7 | 462 | 462.6 | 0.99 | 780–801 |
|   |   |   | B | +93.6° | 102–6 | " | " | 0.93 | 864–924 |
| 5 | " | n-caproic aldehyde | A | +70.1° | 172–9 | 476 | 476.6 | 1.00 | 702–738 |
|   |   |   | B | +97.9° | 180–5 | " | " | 0.93 | 768–828 |
| 6 | " | n-decyl aldehyde | A | +63.6° | 161–4 | 532 | 532.7 | 0.99 | 540–85 |
|   |   |   | B | +91.3° | 147–52 | " | " | 0.93 | 595–648 |
| 7 | & fluocinolone | acetaldehyde | A | +71.1° | 232–5 | 438 | 438.5 | 0.88[1] | 1200–1250 |
|   |   |   | B | +110.8° | 224–7 | " | " | 0.83[1] | 1260–1350 |
| 8 | " | n-butyraldehyde | A | +69.0° | 196–200 | 466 | 466.5 | 0.98 | 1130–1190 |
|   |   |   | B | +94.5° | 169–72 | " | " | 0.93 | 1225–1320 |
| 9 | " | n-caproic aldehyde | A | +65.9° | 143–7 | 494 | 494.6 | 0.98 | 870–930 |
|   |   |   | B | +92.7° | 167–70 | " | " | 0.92 | 960–1015 |
| 10 | " | n-caprylic aldehyde | A | +61.0° | 166–9 | 522 | 522.6 | 0.98 | 735–765 |
|   |   |   | B | +88.2° | 124–7 | " | " | 0.93 | 790–850 |
| 11 | & 11β,16α,17α, 21-tetra-hydroxy-4-pregnene-3,20-dione | acetaldehyde | A | +144.8° | 177–85 | 404 | 404.5 | 0.98 | 396–414 |
|   |   |   | B | +164.6° | 202–10 | " | " | 0.91 | 432–453 |
| 12 | prednacinolone | n-butyraldehyde | A | +85.6° | 225–28 | 430 | 430.5 | 0.99 | 450–68 |
|   |   |   | B | +105.3° | 259–60 | " | " | 0.93 | 510–20 |
| 13 | " | n-caproic aldehyde | A | +72.9° | 198–201 | 458 | 458.6 | 0.99 | 414–32 |
|   |   |   | B | +104.5° | 167–71 | " | " | 0.93 | 462–98 |
| 14 | " | n-caprylic aldehyde | A | +67.6° | 169–73 | 486 | 486.7 | 0.99 | 355–365 |
|   |   |   | B | +96.3° | 143–46 | " | " | 0.93 | 385–400 |
| 15 | " | n-decyl aldehyde | A | +66.0° | 175–66 | 514 | 514.7 | 0.99 | 330–350 |
|   |   |   | B | +93.2° | 124–7 | " | " | 0.93 | 365–385 |

[1]$DMSOD_6$

EXAMPLE 16

Resolution of 16α, 17α-(2′-hydrogen-2′-methyl)-methylenedioxy-11β-hydroxy-21-(benzofurane-2-carbonyloxy)-9-fluorpregna-1,4-diene-3,20-dione into isomers.

A solution of 60 mg pure isomeric mixture of 16α, 17α-(2′-hydrogen-2′-methyl)methylenedioxy-9-fluorpregna-1,4-diene-11α, 21-diol-3,20-dione in 2 ml of dry pyridine was added to 72.2 mg benzofurane-2-carboxylic acid chloride dissolved in 1 ml dry dioxane. The reaction mixture was allowed to stand under stirring at room temperature over night, the major part of the solvents were evaporated in vacuum and the residue was poured into 30 ml of 3% ammonium chloride solution. The precipitate obtained was separated by centrifugation and dissolved in 100 ml of chloroform. The chloroform solution was washed once with 5% sodium carbonate solution, three times with water, dried over magnesium sulphate and evaporated in vacuum. The residue was chromatographed on Sephadex LH-20

(theor. 564.6). Retention volume 300–60 ml.

The isomer purity (>98%) of A and B was determined by NMR-spectroscopy by studying the signal for 18-$CH_3$ positioned at δ = 1.06 ppm ($CDCl_3$) for A and at δ = 1.03 ppm ($CDCl_3$) for B.

Similar separation results have been obtained by using Merckogel OR-PVA 2000, as well as using, in addition to chloroform, methylene chloride, ethylene chloride, ethyl acetate, tetrahydrofurane and dioxane as eluting agents on both types of gel materials.

EXAMPLES 17–28

Different 21-esters of the isomeric mixtures prepared according to Examples 1–15 were prepared analogous to the process described in Example 16. By analogous purification and separation of isomers given below in Table 2 were obtained. The NMR-investigations were carried out in $CDCl_3$.

The acid chlorides used for the esterification are indicated in Table 2 in the following manner. NAC = nicotinic acid chloride, AAC = acetyl chloride, VAC = valeric acid chloride, BAC = benzofurane-2-carboxylic acid chloride.

Table 2

| Ex. No. | the 21-ester of isomeric mixture according to Ex. No. | with | Iso-mer | $[\alpha]_D^{25}$ (c=0.2 in $CH_2Cl_2$)° | Mp °C | Molecular weight found: | Molecular weight calculated: | 18-$CH_3$ δ (ppm) | Retention volume (mls) |
|---|---|---|---|---|---|---|---|---|---|
| 17 | 1 | NAC | A | +121.6° | 268–70 | 525 | 525.6 | 1.07 | 340–65 |
|  |  |  | B | +135.0° | 275–7 | " | " | 1.03 | 375–410 |
| 18 | 1 | VAC | A | +76.6° | 248–51 | 504 | 504.6 | 1.00 | 276–306 |
|  |  |  | B | +102.4° | 261–4 | " | " | 0.97 | 318–354 |
| 19 | 1 | AAC | A | +87.2° | 235–8 | 462 | 462.5 | 0.96 | 325–55 |
|  |  |  | B | +111.0° | 259–63 | " | " | 0.93 | 360–90 |
| 20 | 3 | BAC | A | +139.1° | 135–45 | 592 | 592.7 | 1.07 | 250–75 |
|  |  |  | B | +157.8° | 205–12 | " | " | 1.03 | 280–320 |
| 21 | 3 | NAC | A | +102.0° | 207–10 | 553 | 553.6 | 1.07 | 320–45 |
|  |  |  | B | +132.9° | 252–4 | " | " | 1.04 | 350–80 |
| 22 | 3 | VAC | A | +67.0° | 170–1 | 532 | 532.7 | 1.00 | 255–80 |
|  |  |  | B | +97.7° | 254–6 | " | " | 0.97 | 285–310 |
| 23 | 7 | BAC | A | +143.6° | 147–52 | 582 | 582.6 | 1.06 | 280–320 |
|  |  |  | B | +164.4° | 274–8 | " | " | 1.02 | 325–65 |
| 24 | 7 | AAC | A | +79.7° | 311–4 | 480 | 480.5 | 0.99 | 366–96 |
|  |  |  | B | +101.8° | 322–5 | " | " | 0.95 | 402–38 |
| 25 | 8 | BAC | A | +129.1° | 129–34 | 610 | 610.7 | 1.05 | 270–94 |
|  |  |  | B | +147.8° | 208–10 | " | " | 1.03 | 300–30 |
| 26 | 8 | VAC | A | +66.8° | 212–16 | 550 | 550.7 | 0.98 | 258–82 |
|  |  |  | B | +85.7° | 261–63 | " | " | 0.95 | 288–324 |
| 27 | 12 | AAC | A | +86.2° | 176–9 | 472 | 472.6 | 0.99 | 235–55 |
|  |  |  | B | +97.8° | 183–6 | " | " | 0.96 | 256–75 |
| 28 | 12 | BAC | A | +142.0° | 118–23 | 574 | 574.7 | 1.06 | 200–25 |
|  |  |  | B | +153.6° | 120–30 | " | " | 1.03 | 230–60 |

Below there are given examples of galenic preparations prepared in a conventional manner:

EXAMPLE 29

Ointment, fat anhydrous.

| | | |
|---|---|---|
| Steroid | | 0.001–0.2 |
| Cetanol | | 5 |
| Liquid paraffin | | 20 |
| Vaseline | to | 100 g |

EXAMPLE 30

Cream.

| | | |
|---|---|---|
| Steroid | | 0.001–0.2 |
| Monolein | | 2.5 |
| Wool fat | | 5 |
| Vaseline | | 42 |
| Citric acid | | 0.3 |
| Sodium citrate | | 0.9 |
| Water | to | 100 g |

EXAMPLE 32

Liniment.

| | | |
|---|---|---|
| Steroid | | 0.001–0.2 |
| Cetanol | | 3.2 |
| Stearol | | 0.2 |
| Polyoxyethylene sorbitan monolaurate | | 2 |
| Sorbitan monopalmitate | | 0.5 |
| Propylene glycol | | 4.8 |
| Metagin [a] | | 0.08 |
| Propagin [b] | | 0.02 |
| Water | to | 100 g |

[a] methylester of parahydroxybenzoic acid
[b] propyl ester of parahydroxybenzoic acid

EXAMPLE 32

Tincture.

| | | |
|---|---|---|
| Steroid | | 3–500 mg |
| Ethanol 60 % | to | 100 ml |

EXAMPLE 33

Suspension for injection.

| | | |
|---|---|---|
| Steroid | | 0.05–10 mg |
| Sodium carboxymethyl cellulose | | 7 mg |
| Sodium chloride | | 7 mg |
| Tween 80 [c] | | 0.5 mg |
| Phenyl carbinol | | 8 mg |
| Water, sterile | to | 1 mg |

[c] polyoxyethylene(20)sorbitan monooleate.

EXAMPLE 34

Foam aerosol.

| | | |
|---|---|---|
| Steroid | | 0.001–0.2 |
| Glycerol | | 4 |
| Na-cetyl stearyl alcohol | | 0.2 |
| Cetyl stearyl alcohol | | 3 |
| Isopropylmyristate | | 2 |
| Metagin | | 0.1 |
| Water | | 80 |
| Tetrafluordichloroethane/ difluordichloromethane 40:60 | to | 100 g |

As will be clear from the following presentation of experimental results, one of the stereoisomeric components, component B, has consistently physiologically superior characteristics as compared to the other stereoisomeric component and the stereoisomeric mixture. The stereoisomeric component B being the more active one of the two components A and B in the stereoisomeric pair, may be defined as the stereoisomeric component showing the highest relative rotary power. In connection with gel filtration said component may also be defined as the stereoisomer, which in the gel filtration shows the greatest retention volume, i.e. it leaves last with the eluate. Finally, said active stereoisomeric component may be defined as the component which in NMR-measurements shows the lowest $\delta$-value for 18-$CH_3$. In the following this active stereoisomeric component will always be designated B. As regards the steroids referred to in connection with the present invention the stereoisomeric mixture as well as the individual stereoisomeric components A and B have been investigated with regard to antiinflammatory activity in granulom test on rats subjected to adrenalectomy. The experimental procedure used corresponds largely to that described by G. Engelhardt: Arzneimittel-Forschung, 13, p. 588, 1963. According to this procedure the test substances are applied topically in the implanted cottom wads. It is thereby possible to study the local antinflammatory effect in granulomas and also systemic effects in the form of retrogression of thymus and inhibition of bodyweight growth.

Young male rats of the Sprague-Dawley strain weighing about 110–130 g were subjected to adrenalectomy under ether narcosis. Two sterilized cotton wads of each about 6 mg were implanted simultaneously subcutaneously on the lateral side of the spinal. After awakening the animals were stored 5 per cage and were supplied with normal food and 1% sodium chloride solution as drinking water. On the eighth test day the animals were sacrificed by ether narcosis. The granuloma formed around the cotton wads were carefully recovered and thymus and body weights were measured. The two granuloma from each animal were dried over night at 80° C and weighed. After subtraction of the initial weight of the cotton wads the weight increase was used as a measure of the granulom growth.

The test substances were used dissolved in ethyl acetate. Under aseptic conditions 0.05 ml of said solutions were injected into each of the cottom wads, whereafter the solvent was allowed to evaporate in the desiccator. Normally 3 concentrations of each test substance with the standard doses 3.3, 30 and 270 $\gamma$/animal were investigated. Each test group normally comprised 10 rats. The cotton wads of the control group were injected with only ethyl acetate, but were in other respects treated in the same way. When considering the effects of the test substances the average values of granulom growth, thymus weight and body weight increase day 0–8 were measured in each group in absolute figures and in % of the corresponding figure of the control group. Dose-response curves were drafted and used for estimating the doses giving 50 % reduction of granulom growth and of thymus weight and 25 % decrease of body weight increase.

The results of the experiments carried out with the steroids in question are summarized in Table 3 below. From said table it is immediately clear, that difference in activity is found between the stereoisomeric components in each isomer pair, and that it is always the isomer last eluted from the gel column, which shows the highest activity. By means of the separation process of the present invention it has been possible to show that one of the stereoisomeric components, namely components B, shows a clearly stronger antiinflammatory effect than that obtained with the corresponding stereoisomeric mixture.

Irrespective of the interest to find steroid structures having a high activity there is a great demand for new compounds showing a better relation between antiinflammatory effect and the non-desired systemic effects, that may be observed after the resorption of the compounds. Thymus regression and inhibition of body growth may be seen as examples of such non-desired effects. From the table it is clear that in order to obtain a good antiinflammatory effect (50% inhibition of granulom growth) it is necessary with regard to the reference substances Triamcinolone acetonide and Fluocinolone acetonide to resort to doses of such a level (about 125 and 50 $\gamma$/animal, respectively) as to simultaneously result in a heavy decrease of thymus weight and body weight growth among the test animals. With regard to the compounds of the invention the doses needed for 50 % inhibition of granuloma growth are, however, lower than or possibly of the same level as those giving a thymus regression or body growth inhibition.

Even if component A does not show an antiinflammatory effect as pronounced as that corresponding component B it may in certain cases be more advantageous to use component A as such instead of the isomeric mixture with regard to better characteristics regarding non-desired systemic effects.

Table 3

Table summarizing biological effects of investigated compounds.

| Compound prepared according to Ex. No. | Isomer | Dose ($\gamma$/animal) required to obtain | | |
|---|---|---|---|---|
| | | 50% inhibition of Granuloma growth | Thymus weight | 25% inhibition of Body weight Increase |
| Triamcinolone acetonide | — | 125 | 70 | 100 |
| 1 | A+B | 120 | 270 | >270 |
| 1 | A | 270 | 115 | 60 |
| 1 | B | 30 | 50 | 30 |
| 2 | A+B | 35 | 100 | 140 |
| 2 | A | 25 | 130 | 90 |
| 2 | B | 10 | 60 | 100 |
| 3 | A+B | 10 | >30 | >30 |
| 3 | A | 25 | >30 | >30 |
| 3 | B | 3 | 17 | 100 |
| 4 | A+B | <3 | 70 | 170 |
| 4 | A | <3 | 100 | 170 |
| 4 | B | <3 | 50 | 100 |
| 5 | A+B | 17 | 130 | >270 |
| 5 | A | 30 | 90 | >270 |
| 5 | B | 10 | 90 | >270 |
| Fluocinolone acetonide | — | 50 | 14 | 20 |
| 7 | A | 15 | 12 | 20 |
| 7 | B | 10 | 6 | 15 |
| 8 | A+B | 5 | 10 | 50 |
| 8 | A | 6 | 13 | 50 |
| 8 | B | 4 | 10 | 50 |
| Prednacinolone acetonide | — | 270 | 105 | >270 |
| 12 | A+B | 100 | 80 | 80 |
| 12 | A | 125 | 125 | >270 |
| 12 | B | 40 | 70 | 50 |
| 13 | A+B | 10 | 175 | 90 |
| 13 | A | 8 | >270 | 100 |
| 13 | B | 5 | 210 | >270 |
| 16 | A | 5 | 70 | >45 |
| 16 | B | 3 | 10 | 10 |
| 17 | A | 7 | 45 | 20 |
| 17 | B | 3 | 13 | 20 |
| 18 | A | <3 | 70 | 33 |
| 18 | B | <3 | 10 | 10 |
| 20 | A+B | <3 | 25 | 20 |
| 20 | A | <3 | 90 | 50 |
| 20 | B | <3 | 20 | 5 |
| 21 | A+B | 7 | 35 | 10 |
| 21 | A | <3 | 70 | 70 |
| 21 | B | <3 | 10 | 5 |
| 22 | A+B | 10 | 50 | 30 |
| 22 | A | <3 | 90 | 33 |
| 22 | B | <3 | 35 | 5 |
| 25 | A÷B | <3 | 10 | 10 |
| 25 | A | <3 | 15 | 20 |
| 25 | B | <3 | 7 | 20 |
| 27 | A÷B | <3 | 60 | 40 |
| 27 | A | <3 | 100 | 100 |
| 27 | B | <3 | 60 | 35 |

The compounds may be used to treat inflammation in any living mammalian animal body by administering thereto an effective anti-inflammatory amount of the compound in any suitable form and by any suitable mode of administration, e.g. topically, orally, or parenterally, in the same manner and in the same areas of treatment as their parent compounds, but generally with greater efficiency and therefore generally in lower dosages and according to somewhat lower dosage regimens.

As representative of living animal bodies which may be treated with the compounds and compositions of the invention, and according to the method of treating of the invention, for alleviation of the same and/or similar conditions as those described, the following may be mentioned: domestic animals such as dogs and cats, farm animals such as horses, cows, sheep and goats, to name just a few.

Particularly preferred compounds are the 21-esters of (Reference being had to component A throughout said examples):

Ex. 1.
16α,17α-(2'-hydrogen-2'-methyl)methylenedioxy-9-fluoropregna-1,4-diene-11β,21-diol-3,20-dione.

Ex. 3.
16α,17α-(2'-hydrogen-2'-n-propyl)methylenedioxy-9-fluoropregna-1,4-diene-11β,21-diol-3,20-dione.

Ex. 7.
16α,17α-(2'-hydrogen-2'methyl)methylenedioxy-6α,9-difluoropregna-1,4-diene-11β,21-diol-3,20-dione.

Ex. 8.
16α,17α-(2'-hydrogen-2'-n-propyl)methylenedioxy-6α,9-difluoropregna-1,4-diene-11β,21-diol-3,20-dione.

Ex. 12.
16α,17α-(2'-hydrogen-2'-n-propyl)methylenedioxy-pregna-1,4-diene-11β,21-diol-3,20-dione.

The present application also relates to pharmaceutical formulations or compositions containing the new physiologically-active steroids of the present invention. Such preparations containing the new corticoids of the present invention are intended to be used in local treatment of various inflammatory conditions, where it is well-known that corticoids are effective. Examples of such conditions are most kinds of exzemas and other dermatoses, psoriasis, bronchial asthma, as well as other obstructive lung diseases. (L. Goodman and A. Gilman: The pharmacological basis of therapeutics, Fourth Ed., The Mac Millan Co., London 1970; A. Biedermann Wien, Med. Wochenschr. 121 (1971) 331). Within these areas there is a clinical demand not so much for getting new corticoids with a higher antiinflammatory potency but for compounds with a lower extent of unfavorable systemic side effects. Therefore, the relation between the local and the systemic effects of the new corticoids of the present invention have been investigated in the cotton pellet test and found to be more favorable than for the parent compounds triamcinolone acetonide, fluocinolone acetonide and prednacinolone acetonide, as already set forth in the foregoing.

Depending on where the inflammation is located, different modes of local administration are possible, such as percutaneous, inhalation, parenteral, and rectal, as shown by the following compositions. One important aim of the formulation design is a high biovailability of the active steroid ingredient. In the case of percutaneous formulations, this can be advantageously attained when the steroid is dissolved, with a high thermodynamic activity, in a suitable hydrophilic solution system mainly consisting of a plurality of different pharmaceutically acceptable glycols, e.g., propylene glycol and butandiol-1,3, either alone or in combination with water. The formulation can be in the form of an ointment, a cream, a paste, a liniment, a lotion, a solution or a gel, consisting of a one-phase or two-phase system. In the later case the solution-system with the steroid can make up the disperse as well as the continuous phase. In such a two-phase system there is also present a lipophilic phase consisting of conventional ointment ingredients, such as petrolatum, mineral oil, isopropyl myristate, different waxes, cetanol, steryl alcohol, stearic acid and monoglycerides. Furthermore, the formulation can comprise an emulsifying agent with a suitable HLB* value and in some cases also a preservative.

*HLB = Hydrophile-Lipophile Balance

The following further examples are representative of preparations intended for different modes of local administration. The amount of steroid in the percutaneous formulations is usually 0.001-0.2% by weight, preferably 0.005–0.05% by weight.

Composition 1
Ointment

| | |
|---|---|
| 21-Acetic acid ester of Component A isomer of 16α,17α-(2'-hydrogen-2'-n-propyl)methylenedioxypregna-1,4-diene-11β,21-diol-3,20-dione | 0.025 g |
| Propylene glycol | 9.0 g |
| White wax | 5.0 g |
| Mineral Oil | 16.0 g |
| White petrolatum | 70.0 g |

Composition 2
Cream

| | |
|---|---|
| 21-Acetic acid ester of Component A isomer of 16α,17α-(2'-hydrogen-2'-n-propyl)methylenedioxypregna-1,4-diene-11β,21-diol-3,20-dione | 0.025 g |
| Propylene glycol | q.s.*) |
| Cetomacrogol | 2.0 g |
| Cetosteryl alcohol | 7.0 g |
| Mineral oil | 6.0 g |
| White petrolatum | 15.0 g |
| Chlorcresol | 0.1 g |
| Water | to 100.0 g |

*)amount necessary to dissolve the steroid

Composition 3
Liniment

| | |
|---|---|
| 21-Acetic acid ester of Component A isomer of 16α,17α-(2'-hydrogen-2'-n-propyl)methylenedioxypregna-1,4-diene-11β,21-diol-3,20-dione | 0.025 g |
| Propylene glycol | q.s.*) |
| Cetanol | 3.2 g |
| Steryl alcohol | 0.2 g |
| Polyoxyethylene Sorbitan Monolaurate | 2.0 g |
| Sorbitan Monopalmitate | 0.5 g |
| Methyl hydroxybenzoate | 0.08 g |
| Propyl hydroxybenzoate | 0.02 g |
| water | to 100.0 g |

*)amount necessary to dissolve the steroid

Composition 4
Gel

| | |
|---|---|
| 21-Acetic acid ester of Component A isomer of 16α,17α-(2'-hydrogen-2'-n-propyl)methylenedioxypregna-1,4-diene-11β,21-diol-3,20-dione | 0.025 g |
| Propylene Glycol | 35.0 g |
| Carbopol 934 (TM) *) | 1.0 g |
| Triethanolamine | 1.0 g |
| Methyl hydroxybenzoate | 0.08 g |
| Propyl hydroxybenzoate | 0.02 g |
| Water | to 100.0 g |

*)Carboxyvinyl polymer

Composition 5
Solution

| | |
|---|---|
| 21-Acetic acid ester of Component A isomer of 16α,17α-(2'-hydrogen-2'-n-propyl)methylenedioxypregna-1,4-diene-11β,21-diol-3,20-dione | 0.025 g |
| Isopropanol | 40.0 g |
| Water | to 100.0 g |

Composition 6
Foam Aerosol

| | |
|---|---|
| 21-Acetic acid ester of Component A isomer of 16α,17α-(2'-hydrogen-2'-n-propyl)methylenedioxypregna-1,4-diene-11β,21-diol-3,20-dione | 0.025 g |
| Glycerol | q.s.*) |
| Propylene glycol | q.s.*) |
| Cetylstearyl alcohol | 0.2 g |
| Isopropyl myristate | 2.0 g |
| Methyl hydroxybenzoate | 0.1 g |
| Water | 80.0 g |
| Tetrafluorodichloroethane/Difluorodichloromethane 40:60 | to 100.0 g |

*)amount necessary to dissolve the steroid

Composition 7
Percutaneous Spray

| | |
|---|---|
| 21-Acetic acid ester of Component A isomer of 16α,17α-(2'-hydrogen-2'-n-propyl)methylene-dioxypregna-1,4-diene-11β,21-diol-3,20-dione | 0.025 g |
| Isopropanol | 80.0 g |
| Isopropyl myristate | 10.0 g |
| Trichlorofluoromethane/Dichloro-difluoromethane 50:50 | to 100.0 g |

Composition 8
Suspension for Injection

| | |
|---|---|
| 21-Acetic acid ester of Component A isomer of 16α,17α-(2'-hydrogen-2'-n-propyl)methylene-dioxypregna-1,4-diene-11β,21-diol-3,20-dione | 0.05–10 mg |
| Sodium carboxy methyl cellulose | 7.0 mg |
| Sodium chloride | 7.0 mg |
| Polyoxyethylene(20)sorbitan monooleate | 0.5 mg |
| Phenyl carbinol | 8.0 mg |
| Water, sterile | to 1.0 ml |

COMPOSITION 9

Pressurized Aerosol for Inhalation

Pressurized aerosols containing steroids are intended for oral or nasal inhalation. The aerosol system is arranged so that each measured dose contains 10–1000 μg, preferably 20–250 μg, of the steroid. More active steroids are administered at the lower part of this range.

The micronized steroid contains particles basically less than 5 μm, which are suspended in the propellant mixture by the aid of a surfactant such as sorbitan trioleate, oleic acid, lecithin, or sodium dioctylsulfosuccinate.

| | |
|---|---|
| 21-Acetic acid ester of Component A isomer of 16α,17α-(2'-hydrogen-2'-n-propyl)methylene-dioxypregna-1,4-diene-11β,21-diol-3,20-dione micronized | 0.1 % w/w |
| Sorbitan trioleate | 0.7 % w/w |
| Trichloromonofluoromethane | 24.8 % w/w |
| Dichlorotetrafluoroethane | 24.8 % w/w |
| Dichlorodifluoromethane | 49.6 % w/w |

COMPOSITION 10

Powder Aerosol for Inhalation

The micronized steroid contains particles basically less than 5 μm, which are mixed with a carrier substance such as, for example, lactose. The mixture is dispensed in single unit doses and the powder mixture is inhaled from a suitable powder inhaler. Each single dose contains 10–1000 μg, preferably 20–250 μg of the steroid. More active steroids are administered at the lower part of this range.

| | |
|---|---|
| 21-Acetic acid ester of Compnent A isomer of 16α,17α-(2'-hydrogen-2'-n-propyl)methylene-dioxypregna-1,4-diene-11β,21-diol-3,20-dione micronized | 0.1 mg |
| Lactose | 50.0 mg |

The new physiologically active steroids can of course also be given orally, e.g., in a single dose of 0.1–10mg, preferably 0.5–2.5 mg, especially in a daily dose of 0.5–20 mg.

Composition 11 Tablets
Each tablet contains:

| | |
|---|---|
| Steroid | 0.1–10 mg |
| Maize Starch | 25.0 mg |
| Lactose | 190.0 mg |
| Gelatin | 1.5 mg |
| Talc | 12.0 mg |
| Magnesium stearate | 1.5 mg |

For some types of inflammation, it can be of advantage to combine the steroid with other active substances such as local analgetics and antibiotics, as illustrated by the following compositions.

Composition 12
Rectal Ointment

| | |
|---|---|
| 21-Acetic acid ester of Component A isomer of 16α,17α-(2'-hydrogen-2'-n-propyl)methylene-dioxypregna-1,4-diene-11β,21-diol-3,20-dione | 0.5 mg |
| Lidocaine | 25.0 mg |
| Mineral Oil | 0.2 g |
| White petrolatum | to 1.0 g |

Composition 13
Suppository

| | |
|---|---|
| 21-Acetic acid ester of Component A isomer of 16α,17α-(2'-hydrogen-2'-n-propyl)methylene-dioxypgrena-1,4-diene-11β,21-diol-3,20-dione | 1 mg |
| Lidocaine | 60 mg |
| Massa supp Imhausen | q.s. |

Composition 14
Ointment with Steroid + Antibioticum

| | |
|---|---|
| 21-Acetic acid ester of Component A isomer of 16α,17α-(2'-(2'-n-propyl)methylene dioxypregna-1,4-diene-11β,21-diol-3,20-dione | 0.025 g |
| Neomycin sulfate | 0.5 g |
| Propylene glycol | 9.0 g |
| White wax | 5.0 g |
| Mineral oil | 16.0 g |
| White petrolatum | 70.0 g |

The following Table 4 discloses the results of the cotton-pellet test hereinbefore described, giving in addition figures for the therapeutic ratios, that is, the ratios of the $ED_{50}$ for thymus weight inhibition divided by the $ED_{50}$ for granuloma formation inhibition, and the $ED_{25}$ for body weight increase inhibition over the $ED_{50}$ for granuloma formation inhibition. As will be recognized, the higher the number for the therapeutic ratio, the more favorable the therapeutic ratio. Table 4 shows that, for the Component B esters, a relatively low therapeutic ratio prevails, whereas for the corresponding Component A esters, a relatively high therapeutic ratio prevails. A comparison of the therapeutic ratios given in the last two columns of Table 4 shows that, for the esters of the eight (8) examples noted in that table, the Component A esters have a therapeutic ratio which is greatly in excess of and therefore more favorable than the therapeutic ratio for the corresponding Component B esters. As will be noted for the table, the therapeutic ratio for thymus over granuloma for the Component A esters is 4.2, 7.1, 4.5, 2.6, 2.2, 1.7, 2.5 and 1.7 times as good as it is for the corresponding Component B ester isomer, whereas the therapeutic ratio for the Component A ester isomer as far as body weight over granuloma 2.7, 3.3, 9.8, 6.4, 2.3, 2.8, 3.3 and 2.8 times as favorable as for the corresponding Component B ester isomer. That the Component A ester isomers, compositions thereof, and the method of treating therewith, which is the subject matter claimed in the present application, are superior to the Component B ester isomers and their corresponding compositions and treatment method from a therapeutic ratio standpoint is clear from the data given in Table 4 and summarized in the foregoing.

TABLE 4

| Ester prepared according to ex. no. | Isomer | Cotton-pellet test | | | Therapeutic ratio | |
|---|---|---|---|---|---|---|
| | | ED$_{50}$ granuloma formation inhibition | ED$_{50}$ thymus weight inhibition | ED$_{25}$ body weight increase inhibition | thymus / granuloma | body weight / granuloma |
| 16 | A | 5 | 70 | >45 | 14.0 | >9.0 |
| | B | 3 | 10 | 10 | 3.3 | 3.3 |
| 18 | A | <3 | 70 | 33 | >23.3 | >11.0 |
| | B | <3 | 10 | 10 | >3.3 | >3.3 |
| 20 | A | <3 | 90 | 50 | >30.0 | >16.7 |
| | B | <3 | 20 | 5 | >6.7 | >1.7 |
| 22 | A | <3 | 90 | 33 | >30.0 | >11.0 |
| | B | <3 | 35 | 3 | >11.7 | >1.7 |
| 25 | A | <3 | 15 | 20 | >5.0 | >6.7 |
| | B | <3 | 7 | 20 | >2.3 | >2.9 |
| 27 | A | <3 | 100 | 100 | >33.3 | >33.3 |
| | B | <3 | 60 | 35 | >20.0 | >11.7 |
| 23 | A | <3 | 10 | 10 | >3.3 | >3.3 |
| | B | <3 | 4 | 3 | >1.3 | >1.0 |
| 28 | A | <3 | 100 | 100 | >33.3 | >33.3 |
| | B | <3 | 60 | 35 | >20.0 | >11.7 |

The preferred compounds according to the present invention are, and the preferred compositions and method of treating according to the present invention employ as active ingredient, the 21-acetates of the Component A isomer of the 16α,17α derivatives of fluocinolone, triamcinolone, and prednacinolone, all having a 2'-hydrogen and a 2'-methyl, ethyl, or n-propyl group, namely, the 21-acetates of the Component A isomers of 16α,17α-(2'-hydrogen-2'-Q)-methylenedioxy-9-fluorpregna-1,4-diene-11β,21-diol-3,20-dione; 16α,-17α-(2'-hydrogen-2'-Q)methylenedioxy-6α,9-difluoropregna-1,4-diene-11β,21-diol-3,20-dione; 16α,17α-(2'-hydrogen-2'-Q-methylenedioxypregna-1,4-diene-11β,21-diol-3,20-dione, wherein Q is selected from the group consisting of methyl, ethyl, and n-propyl. The prednacinolone and triamcinolone derivative Component A 21-acetates are especially preferred. Least preferred among the esters named are the pyridine-3-carboxylates and the pyridine-4-carboxylates.

Various modifications in the compounds, compositions, and methods of the invention will be apparent to one skilled in the art and may be made without departing from the spirit or scope thereof, and it is therefore to be understood that the invention is to be limited only by the scope of the appended claims.

We claim:

1. Stereoisomeric Component A of a stereoisomeric mixture (isomeric pair) of a steroid having the general formula:

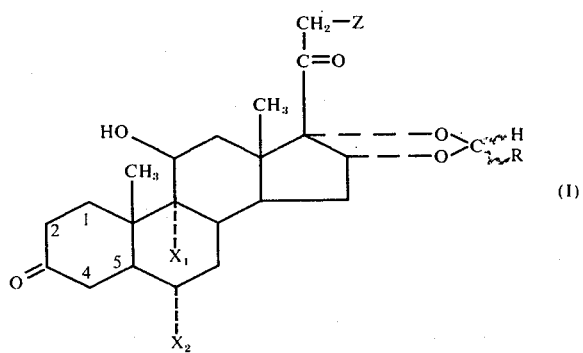

(I)

wherein the 1,2-position is saturated or a double bond is present in that position, a double bond always being present in at least the 4,5-position, $X_1$ and $X_2$ are independently selected from hydrogen and fluorine, $X_1$ being selected from hydrogen and fluorine when $X_2$ is hydrogen and $X_1$ being fluorine when $X_2$ is fluorine, Z is esterified hydroxyl wherein the hydroxyl group is esterified with a member of the group consisting of phosphoric and sulphuric acids, dicarboxylic acids having two to twelve carbon atoms, inclusive, pyridine-3-carboxylic acid, pyridine-4-carboxylic acid, benzofurane-2-carboxylic acid, and menthoxymethylcarboxylic acid, and lower alkanoic acids, and R is selected from alkyl groups with straight or branched hydrocarbon chains, having one to ten carbon atoms, inclusive, said Component A being the isomer of the isomer pair showing the lowest relative rotary power or having the smallest retention volume in gel filtration using a cross-linked dextran gel.

2. Stereoisomeric Component A according to claim 1 characterized in that R is an alkyl group having one to six carbon atoms, inclusive.

3. Stereoisomeric Component A according to claim 1, wherein Z is hydroxyl esterified with an acid selected from acetic acid, propionic acid, butyric acid, valeric acid, isovaleric acid, trimethyl acetic acid, hexanoic acid, tert.-butylacetic acid, and octanoic acid.

4. Stereoisomeric Component A according to claim 1, wherein Z is hydroxyl esterified with an acid selected from pyridine-3-carboxylic acid, pyridine-4-carboxylic acid, benzofurane-2-carboxylic acid, and menthoxymethylcarboxylic acid.

5. Stereoisomeric Component A according to claim 1, wherein Z is hydroxyl esterified with an acid selected from dicarboxylic acids having two to twelve carbon atoms inclusive.

6. Stereoisomeric Component A according to claim 1, wherein Z is hydroxyl esterified with an acid selected from phosphoric and sulphuric acids.

7. Stereoisomeric Component A according to claim 1, which is 16α,17α-(2'-methyl)methylenedioxy-9-fluoropregna-1,4-diene-11β,21-diol-3,20-dione 21-acetate.

8. Stereoisomeric Component A according to claim 1, which is 16α,17α-(2'-hydrogen-2'-methyl)methylenedioxy-9-fluoropregna-1,4-diene-11β,21-diol-3,20-dione 21-valerate.

9. Stereoisomeric Component A according to claim 1, which is 16α,17α-(2'-hydrogen-2'-n-propyl)methylenedioxy-9-fluoropregna-1,4-diene-11β,21-diol-3,20-dione 21-acetate.

10. Stereoisomeric Component A according to claim 1, which is 16α,17α-(2'-hydrogen-2'-n-propyl)methylenedioxy-9-fluoropregna 1,4-diene-11β,21-diol-3,20-dione 21-valerate.

11. Stereoisomeric Component A according to claim 1, which is 16α,17α-(2'-hydrogen-2'-methyl)methylenedioxy-6α,9-difluoropregna-1,4-diene-11β,21-diol-3,20-dione 21-acetate.

12. Stereoisomeric Component A according to claim 1, which is 16α,17α-(2'-hydrogen-2'-n-propyl)methylenedioxy-6α,9-difluoropregna-1,4-diene-11β,21-diol-3,20-dione 21-acetate.

13. Stereoisomeric Component A according to claim 1, which is 16α,17α-(2'-hydrogen-2'-n-propyl)methylenedioxypregna-1,4-diene-11β,21-diol-3,20-dione 21-acetate.

14. Stereoisomeric Component A according to claim 1, which is 16α,17α-(2'-hydrogen-2'-methyl)methylenedioxypregna-1,4-diene-11β,21-diol-3,20-dione 21-acetate.

15. Stereoisomeric Component A according to claim 1, which 16α,17α-(2'-hydrogen-2'-methyl)methylenedioxy-9-fluoropregna-1,4-diene-11β,21-diol-3,20 dione; 16α,17α-(2'-hydrogen-2'-n-propyl)methylenedioxy-9-fluoropregna-1,4-diene-11β,21-diol-3,20-dione; 16α,17α-(2'-hydrogen-2'-methyl)methylenedioxy-6α,9-difluoropregna-1,4-diene-11β,21-diol-3,20-dione; 16α,17α-(2'-hydrogen-2'-n-propyl)methylenedioxy-6α,9-difluoropregna-1,4-diene-11β,21-diol-3,20dione; or 16α,17α-(2'-hydrogen-2'-n-propyl)-methylenedioxypregna-1,4-diene-11β,21-diol-3,20-dione, wherein the 21hydroxyl is esterified with an acid selected from the group consisting of acetic acid, propionic acid, butyric acid, valeric acid, isovaleric acid, trimethyl acetic acid, hexanoic acid, tert.-butylacetic acid, octanoic acid; pyridine-3carboxylic acid, pyridine-4-carboxylic acid, benzofurane-2-carboxylic acid, methoxymethylcarboxylic acid; dicarboxylic acids having two to twelve carbon atoms, inclusive; phosphoric acid and sulphuric acid.

16. A pharmaceutically-active composition, suitable for use in the treatment of inflammation, containing as active ingredient an effective antiinflammatory amount of a steroid compound, in combination with a pharmaceutically-acceptable carrier, said steroid compound being the stereoisomeric Component A of a stereoisomeric mixture (isomeric pair) of a 2'-unsymmetrical 16,17-methylenedioxy steriod having the general formula:

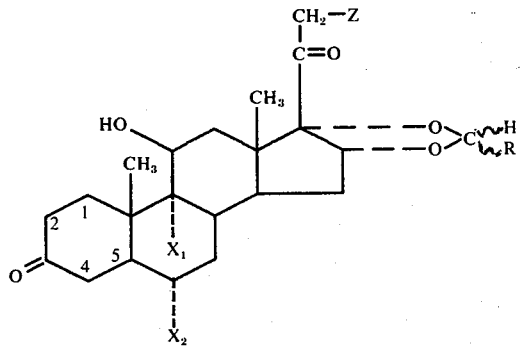

(I)

wherein the 1,2-position is saturated or a double bond is present in that position, a double bond always being present in at least the 4,5-position, $X_1$ and $X_2$ are independently selected from hydrogen and fluorine, $X_1$ being selected from hydrogen and fluorine when $X_2$ is hydrogen and $X_1$ being fluorine when $X_2$ is fluorine, Z is esterified hydroxyl wherein the hydorxyl group is esterified with a member of the group consisting of phosphoric and sulphuric acids, dicarboxylic acids having two to twleve carbon atoms, inclusive, pyridine-3-carboxylic acid, pyridine-4-carboxylic acid, benzofurane-2-carboxylic acid, and menthoxymethylcarboxylic acid, and lower alkanoic acids, and R is selected from alkyl groups with straight or branched hydrocarbon chains, having one to ten carbon atoms, inclusive, said Component A being the isomer of the isomer pair showing the lowest relative rotary power or having the smallest retention volume in gel filtration using a cross-linked dextran gel.

17. The composition of claim 16, wherein R in the active ingredient is selected from straight and branched hydrocarbon chains having one to six carbon atoms, inclusive.

18. The composition of claim 16, wherein $X_1$ in the active ingredient is fluorine.

19. The composition of claim 16, wherein $X_2$ in the active ingredient is fluorine.

20. The composition of claim 16, wherein Z in the active ingredient is hydroxyl esterified with an acid selected from acetic acid, propionic acid, butyric acid, valeric acid, isovaleric acid, trimethylacetic acid, hexanoic acid, tert.butylacetic acid, and octanoic acid.

21. The composition of claim 16, wherein Z in the active ingredient is hydroxyl esterified with an acid selected from pyridine-3-, pyridine-4-, benzofurane-2-carboxylic acid, and menthoxymethylcarboxylic acid.

22. The composition of claim 16, wherein Z in the active ingredient is hydroxyl esterified with an acid selected from dicarboxylic acids having two to twelve carbon atoms, inclusive.

23. The composition of claim 16, wherein Z in the active ingredient is hydroxyl esterified with an acid selected from phosphoric and sulphuric acids.

24. The composition of claim 16, wherein the stereoisomeric Component A active ingredient is selected from the group consisting of the stereoisomeric Component A of 16α,17α-(2'-hydrogen-2'-methyl)methylenedioxy-9-fluoropregna-1,4-diene-11β,21-diol-3,20 dione; 16β,17β-(2'-hydrogen-2'-n-propyl)methylenedioxy-9-fluoropregna-1,4-diene-11β,21-diol-3,20-dione; 16α,17α-(2'-hydrogen-2'-methyl)methylenedioxy-6α,9-difluoropregna-1,4-diene-11β,21-diol-3,20-dione; 16α,17α-(2'-hydrogen-2'-n-propyl)methylenedioxy-6α,9-difluoropregna-1,4-diene-11β,21-diol-3,20-dione; 16α,17α-(2'-hydrogen-2'-n-propyl)methylenedioxy-6α,9-difluoropregna-1,4-diene-11β,21-diol-3,20dione; or 16α,17α-(2'-hydrogen-2'-n-propyl)-methylenedioxypregna-1,4-diene-11β,21-diol-3,20-dione, wherein the 21-hydroxyl is esterified with an acid selected from the group consisting of acetic acid, propionic acid, butyric acid, valeric acid, isovaleric acid, trimethylacetic acid, hexanoic acid, tert.-butylacetic acid, octanoic acid; pyridine-3-carboxylic acid, pyridine-4-carboxylic acid, benzofurane-2-carboxylic acid, menthoxymethylcarboxylic acid; dicarboxylic acids having two to twelve carbon atoms, inclusive; phosphoric acid and sulphuric acid.

25. The composition of claim 16, in the form of an ointment.

26. The composition of claim 16, wherein the active steroid ingredient is dissolved in a hydrophilic solution system.

27. The composition of claim 16, wherein the system comprises a plurality of different pharmaceutically-acceptable glycols.

28. The composition of claim 16, wherein the composition is a percutaneous formulation for local administration, wherein the amount of active steroid ingredient is between 0.001 and 0.2 percent by weight.

29. The composition of claim 16, wherein the composition is a percutaneous formulation for local administration, wherein the amount of active steroid ingredient is between 0.005 and 0.05 percent by weight.

30. The composition of claim 16, wherein the composition is in a form suitable for inhalation administration.

31. The composition of claim 16, wherein the active steroid ingredient is the stereoisomeric Component A of the 21-acetate ester of a compound selected from the group consisting of 16α,17α-(2'-hydrogen-2'-Q)-methylenedioxy-9-fluorpregna-1,4-diene-11β,21-diol-3,20-dione; 16α,17α-(2'-hydrogen-2'-Q)methylenedioxy-6α,9-difluoropregna-1,4-diene-11β,21-diol-3,20-dione; and 16α,17α-(2'-hydrogen-2'-Q)methylenedioxypregna-1,4-diene-11β,21-diol-3,20-dione, wherein Q is selected from the group consisting of methyl, ethyl and n-propyl.

32. A method of treating inflammation in a mammalian body in need of such treatment comprising the step of administering thereto an effective antiinflammatory amount of the stereoisomeric Component A of a 2'-unsymmetrical 16,17-methylenedioxy steroid having the general formula I as defined in claim 1.

33. The method of claim 32, wherein the active antiinflammatory steroid is administered in the form of a pharmaceutically-active composition in combination with a pharmaceutically-acceptable carrier therefor.

34. The method of claim 32, wherein R in the said steroid is selected from straight and branched hydrocarbon chains having one to six carbon atoms, inclusive.

35. The method of claim 32, wherein $X_1$ in the said steroid is fluorine.

36. The method of claim 32, wherein $X_2$ in the said steroid is fluorine.

37. The method of claim 32, wherein Z in the said steroid is hydroxyl esterified with an acid selected from acetic acid, propionic acid, butyric acid, valeric acid, isovaleric acid, trimethylacetic acid, hexanoic acid, tert.-butyl acetic acid, and octanoic acid.

38. The method of claim 32, wherein Z in the said steroid is hydroxyl esterified with an acid selected from pyridine-3-, pyridine-4-, benzofurane-2-carboxylic acid, and menthoxymethylcarboxylic acid.

39. The method of claim 32, wherein Z in the said steroid is hydroxyl esterified with an acid selected from dicarboxylic acids having two to twelve carbon atoms, inclusive.

40. The method of claim 32, wherein Z in the said steroid is hydroxyl esterified with an acid selected from phosphoric and sulphuric acids.

41. The method of claim 32, wherein the stereoisomeric Component A active ingredient is selected from the group consisting of the stereoisomeric Component A of 16α,17α-(2'-hydrogen-2'-methyl)methylenedioxy-9-fluoropregna-1,4-diene-11β,21-diol-3,20 dione; 16α,17α-(2'-hydrogen-2'-n-propyl)methylenedioxy-9-fluoropregna-1,4-diene-11β,21-diol- 3,20-dione; 16α,17α-(2'-hydrogen-2'-methyl)methylenedioxy-6α,9-difluoropregna-1,4-diene-11β,21-diol-3,20-dione; 16α,17α-(2'-hydrogen-2'-n-propyl)methylenedioxy-6α,9-difluoropregna-1,4-diene-11β,21-diol-3,20dione; or 16α,17α-(2'-hydrogen-2'-n-propyl)-methylenedioxypregna-1,4-diene-11β,21-diol-3,20-dione, wherein the 21-hydroxyl is esterified with an acid selected from the group consisting of acetic acid, propionic acid, butyric acid, valeric acid, isovaleric acid, trimethyl acetic acid, hexanoic acid, tert.-butylacetic acid, octanoic acid; pyridine-3-carboxylic acid, pyridine-4-carboxylic acid, benzofurane-2-carboxylic acid, menthoxymethylcarboxylic acid; dicarboxylic acids having two to twelve carbon atoms, inclusive; phosphoric acid and sulphuric acid.

42. The method of claim 32, wherein the active antiinflammatory steroid is administered in the form of an ointment.

43. The method of claim 32, wherein the active antiinflammatory steroid is administered dissolved in a hydrophilic solution system.

44. The method of claim 43, wherein the system comprises a plurality of different pharmaceutically-acceptable glycols.

45. The method of claim 32, wherein the active antiinflammatory steroid is administered in the form of a percutaneous pharmaceutically-active composition in combination with a pharmaceutically-acceptable carrier therefor wherein the amount of active steroid ingredient is between 0.001 and 0.2 percent by weight.

46. The method of claim 32, wherein the active antiinflammatory steroid is administered in the form of a pharmaceutically-active composition in combination with a pharmaceutically-acceptable carrier therefor, wherein the composition is a percutaneous formulation for local administration, and wherein the amount of active steroid ingredient in said composition is between 0.005 and 0.05 percent by weight.

47. The method of claim 32, wherein the active antiinflammatory steroid is administered by inhalation.

48. The method of claim 32, wherein the active steroid ingredient is the stereoisomeric Component A of the 21-acetate ester of a compound selected from the group consisting of 16α,17α-(2'-hydrogen-2'-Q)methylenedioxy-9-fluoropregna-1,4-diene-11β,21-diol-3,20-dione; 16α,17α-(2'-hydrogen-2'-Q)methylenedioxy-6α,9-difluoropregna-1,4-diene-11β,21-diol-3,20-dione; and 16α,17α-(2'-hydrogen-2'-Q)methylenedioxypregna-1,4-diene-11β,21-diol-3,20-dione, wherein Q is selected from the group consisting of methyl, ethyl and n-propyl.

49. The composition of claim 16, wherein the composition is an aerosol formulation for oral or nasal administration and wherein the amount of active steroid ingredient in said formulation is adapted to provide between about 10 and 1,000 μg per unit dose.

50. The composition of claim 16, wherein the composition is an aerosol formulation for oral or nasal administration and wherein the amount of active steroid ingredient in said formulation is adapted to provide between about 20 and 250 μg per unit dose.

51. The method of claim 32, wherein the active antiinflammatory steroid is administered in the form of an aerosol composition for oral or nasal inhalation and wherein said active steroid is administered in an amount between about 10 and 1,000 μg per unit dose.

52. The method of claim 32, wherein the active antiinflammatory steroid is administered in the form of an aerosol composition for oral or nasal inhalation and wherein said active steroid is administered in an amount between about 20 and 250 μg per unit dose.

53. The composition of claim 16, wherein the composition is an oral unit dosage form containing between about 0.1 and 10 milligrams per unit dose of the active steroid ingredient.

54. The composition of claim 16, wherein the composition is an oral unit dosage form containing between about 0.5 and 2.5 milligrams per unit dose of the active steroid ingredient.

55. The method of claim 32, wherein the active antiinflammatory steroid is administered orally in a unit dosage form containing between about 0.1 and 10 milligrams of said active antiinflammatory steroid per unit dose.

56. The method of claim 32, wherein the active antiinflammatory steroid is administered orally in a unit dosage form containing between about 0.5 and 2.5 milligrams of said active antiinflammatory steroid per unit dose.

57. The method of claim 32, wherein the active antiinflammatory steroid is administered in an oral dosage form in an amount between about 0.5 and 20 milligrams per daily dose.

58. The method of claim 57, wherein the active steroid ingredient is the stereoisomeric Component A of the 21-acetate ester of a compound selected from the group consisting of $16\alpha,17\alpha$-(2'-hydrogen-2'-Q)methylenedioxy-9-fluoropregna-1,4-diene-11$\beta$,21-diol-3,20-dione; $16\alpha,17\alpha$-(2'-hydrogen-2'-Q)methylenedioxy-6$\alpha$,9-difluoropregna-1,4-diene-11$\beta$,21-diol-3,20-dione; and $16\alpha,17\alpha$-(2'-hydrogen-2'-Q)methylenedioxypregna-1,4-diene-11$\beta$,21-diol-3,20-dione, wherein Q is selected from the group consisting of methyl, ethyl and n-propyl.

59. The method of claim 45, wherein the active steroid ingredient is the stereoisomeric Component A of the 21-acetate ester of a compound selected from the group consisting of $16\alpha,17\alpha$-(2'-hydrogen-2'-Q)methylenedioxy-9-fluoropregna-1,4-diene-11$\beta$,21-diol-3,20-dione; $16\alpha,17\alpha$-(2'-hydrogen-2'-Q)methylenedioxy $6\alpha,9$-difluoropregna-1,4-diene-11$\beta$,21-diol-3,20-dione; and $16\alpha,17\alpha$-(2'-hydrogen-2'-Q)methylendioxypregna-1,4-diene-11$\beta$,21-diol-3,20-dione, wherein Q is selected from the group consisting of methyl, ethyl and n-propyl.

60. The method of claim 51, wherein the active steroid ingredient is the stereoisomeric Component A of the 21-acetate ester of a compound selected from the group consisting of $16\alpha,17\alpha$-(2'-hydrogen-2'-Q)methylenedioxy-9-fluoropregna-1,4-diene-11$\beta$,21-diol-3,20-dione; $16\alpha,17\alpha$-(2'-hydrogen-2'-Q)methylenedioxy-6$\alpha$,9-difluoropregna-1,4-diene-11$\beta$,21-diol-3,20-dione, and $16\alpha,17\alpha$-(2'-hydrogen-2'-Q)methylenedioxypregna-1,4-diene-11$\beta$, 21-diol-3,20-dione, wherein Q is selected from the group consisting of methyl, ethyl and n-propyl.

61. The stereoisomeric Component A of the 21-acetate ester of a compound selected from the group consisting of $16\alpha,17\alpha$-(2'-hydrogen-2'-Q)methylenedioxy-9-fluoropregna-1,4-diene-11$\beta$,21-diol-3,20-dione; $16\alpha,17\alpha$-(2'-hydrogen-2'-Q)methylenedioxy-6$\alpha$,9-difluoropregna-1,4-diene-11$\beta$,21-diol-3,20dione; and $16\alpha,17\alpha$-(2'-hydrogen-2'-Q)methylenedioxypregna-1,4-diene-11$\beta$,21-diol-3,20-dione, wherein Q is selected from the group consisting of methyl, ethyl and n-propyl.

\* \* \* \* \*

UNITED STATES PATENT OFFICE
CERTIFICATE OF CORRECTION

Patent No. 3,996,359            Dated December 7, 1976

Inventor(s) Ralph Lennart Brattsand, et al

It is certified that error appears in the above-identified patent and that said Letters Patent are hereby corrected as shown below:

Column 1, line 44; change "and therefore" to read ---are therefore---.

Column 5, in Table 1, under heading "MP(°C)" Ex. 15; change "175-66" to read ---157-66---.

Column 6, line 61; change "of isomers" to read ---the isomers---.

Column 7, line 55; change "EXAMPLE 32" to read ---EXAMPLE 31---.

Column 9, line 39; change "cottom wads" to read ---cotton wads---.

Column 16, line 58; change "(2'-methyl)" to read ---(2'-hydrogen-2'-methyl)---.

Column 18, line 45; change "16β,17β" to read ---16α,17α---.

Column 18, lines 51-53; delete in their entirety and rewrite as follows ---3,20-dione; or 16α,17α-(2'-hydrogen-2'-n-propyl)- ---.

Column 20, line 3; change ""3,20dione" to read ---3,20-dione---.

Column 22, line 28; change "3,20dione" to read ---3,20-dione---.

Signed and Sealed this

Sixth Day of September 1977

[SEAL]

Attest:

RUTH C. MASON        LUTRELLE F. PARKER
*Attesting Officer*      *Acting Commissioner of Patents and Trademarks*